(12) United States Patent
Voronenko et al.

(10) Patent No.: US 11,406,846 B2
(45) Date of Patent: Aug. 9, 2022

(54) METHODS FOR RADIATION DELIVERY IN EMISSION-GUIDED RADIOTHERAPY

(71) Applicant: RefleXion Medical, Inc., Hayward, CA (US)

(72) Inventors: Yevgen Voronenko, Sunnyvale, CA (US); Rostem Bassalow, Hayward, CA (US); Peter Olcott, Los Gatos, CA (US); Brent Harper, Pescadero, CA (US); David Larkin, Menlo Park, CA (US)

(73) Assignee: RefleXion Medical, Inc., Hayward, CA (US)

( * ) Notice: Subject to any disclaimer, the term of this patent is extended or adjusted under 35 U.S.C. 154(b) by 580 days.

(21) Appl. No.: 16/412,780

(22) Filed: May 15, 2019

(65) Prior Publication Data

US 2019/0262630 A1    Aug. 29, 2019

Related U.S. Application Data

(63) Continuation of application No. PCT/US2017/061728, filed on Nov. 15, 2017.
(Continued)

(51) Int. Cl.
*A61B 6/03*       (2006.01)
*A61N 5/10*       (2006.01)
(Continued)

(52) U.S. Cl.
CPC ........... *A61N 5/1049* (2013.01); *A61B 6/037* (2013.01); *A61B 6/12* (2013.01); *A61B 6/5205* (2013.01);
(Continued)

(58) Field of Classification Search
CPC .... A61N 2005/1052; A61N 2005/1085–1098; A61N 5/103–1084;
(Continued)

(56) References Cited

U.S. PATENT DOCUMENTS

| 3,794,840 A | 2/1974 | Scott |
| 3,906,233 A | 9/1975 | Vogel |

(Continued)

FOREIGN PATENT DOCUMENTS

| CN | 1681436 A | 10/2005 |
| CN | 1960780 A | 5/2007 |

(Continued)

OTHER PUBLICATIONS

Shalchian, B., Rajabi, H. and Soltanian-Zadeh, H., 2009. Assessment of the Wavelet Transform in Reduction of Noise from Simulated PET Images. Journal of Nuclear Medicine Technology, 37(4), pp. 223-228. (Year: 2009).*
(Continued)

*Primary Examiner* — Thaddeus B Cox
*Assistant Examiner* — Marc D. Honrath
(74) *Attorney, Agent, or Firm* — Cooley LLP

(57) ABSTRACT

This application relates to methods for delivering radiation to a positron-emitting target within a subject under continuous PET guidance. Instead of directing radiation at a collinear path along each detected positron line-of-response (LOR), the methods generally include detecting a pattern of LORs that intersect the target. In response to the pattern, radiation may be delivered along paths that are not necessarily collinear to any of the LORs. Methods for further modifying radiation delivery as well as the detected LOR population are also described.

30 Claims, 8 Drawing Sheets

Related U.S. Application Data

(60) Provisional application No. 62/422,276, filed on Nov. 15, 2016.

(51) Int. Cl.
*A61B 6/00* (2006.01)
*A61B 6/12* (2006.01)
*G06T 11/00* (2006.01)

(52) U.S. Cl.
CPC .......... *A61N 5/1037* (2013.01); *A61N 5/1081* (2013.01); *G06T 11/008* (2013.01); *A61B 6/032* (2013.01); *A61N 2005/1052* (2013.01)

(58) Field of Classification Search
CPC ............... G06T 11/00; G06T 11/003; G06T 11/005–008; A61B 6/03; A61B 6/032; A61B 6/037; A61B 6/12; A61B 6/52; A61B 6/5205; A61B 6/5258; A61B 6/5264; A61B 6/5282; A61B 6/5294
See application file for complete search history.

(56) References Cited

U.S. PATENT DOCUMENTS

| | | | |
|---|---|---|---|
| 4,389,569 A | 6/1983 | Hattori et al. |
| 4,503,331 A | 3/1985 | Kovacs, Jr. et al. |
| 4,529,882 A | 7/1985 | Lee |
| 4,563,582 A | 1/1986 | Mullani |
| 4,575,868 A | 3/1986 | Ueda et al. |
| 4,642,464 A | 2/1987 | Mullani |
| 4,647,779 A | 3/1987 | Wong |
| 4,677,299 A | 6/1987 | Wong |
| 4,868,844 A | 9/1989 | Nunan |
| 5,015,851 A | 5/1991 | Singh et al. |
| 5,075,554 A | 12/1991 | Yunker et al. |
| 5,206,512 A | 4/1993 | Iwao |
| 5,207,223 A | 5/1993 | Adler |
| 5,317,616 A | 5/1994 | Swerdloff et al. |
| 5,329,567 A | 7/1994 | Ikebe |
| 5,351,280 A | 9/1994 | Swerdloff et al. |
| 5,390,225 A | 2/1995 | Hawman |
| 5,394,452 A | 2/1995 | Swerdloff et al. |
| 5,396,534 A | 3/1995 | Thomas |
| 5,418,827 A | 5/1995 | Deasy et al. |
| 5,442,675 A | 8/1995 | Swerdloff et al. |
| 5,647,663 A | 7/1997 | Holmes |
| 5,724,400 A | 3/1998 | Swerdloff et al. |
| 5,751,781 A | 5/1998 | Brown et al. |
| 5,813,985 A | 9/1998 | Carroll |
| 5,818,902 A | 10/1998 | Yu |
| 5,851,182 A | 12/1998 | Sahadevan |
| 5,937,028 A | 8/1999 | Tybinkowski et al. |
| 6,180,943 B1 | 1/2001 | Lange |
| 6,184,530 B1 | 2/2001 | Hines et al. |
| 6,188,748 B1 | 2/2001 | Pastyr et al. |
| 6,239,438 B1 | 5/2001 | Schubert |
| 6,260,005 B1 | 7/2001 | Yang et al. |
| 6,281,505 B1 | 8/2001 | Hines et al. |
| 6,385,288 B1 | 5/2002 | Kanematsu |
| 6,438,202 B1 | 8/2002 | Olivera et al. |
| 6,449,331 B1 | 9/2002 | Nutt et al. |
| 6,449,340 B1 | 9/2002 | Tybinkowski et al. |
| 6,455,856 B1 | 9/2002 | Gagnon |
| 6,473,634 B1 | 10/2002 | Barni |
| 6,504,899 B2 | 1/2003 | Pugachev et al. |
| 6,552,693 B1 | 4/2003 | Leisten |
| 6,560,311 B1 | 5/2003 | Shepard et al. |
| 6,618,467 B1 | 9/2003 | Ruchala et al. |
| 6,661,866 B1 | 12/2003 | Limkeman et al. |
| 6,696,694 B2 | 2/2004 | Pastyr et al. |
| 6,700,949 B2 | 3/2004 | Susami et al. |
| 6,714,620 B2 | 3/2004 | Caflisch et al. |
| 6,730,924 B1 | 5/2004 | Pastyr et al. |
| 6,735,277 B2 | 5/2004 | McNutt et al. |
| 6,794,653 B2 | 9/2004 | Wainer et al. |
| 6,810,103 B1 | 10/2004 | Tybinkowski et al. |
| 6,831,961 B1 | 12/2004 | Tybinkowski et al. |
| 6,865,254 B2 | 3/2005 | Näfstadius |
| 6,888,919 B2 | 5/2005 | Graf |
| 6,914,959 B2 | 7/2005 | Bailey et al. |
| 6,934,363 B2 | 8/2005 | Seufert |
| 6,965,661 B2 | 11/2005 | Kojima et al. |
| 6,976,784 B2 | 12/2005 | Kojima et al. |
| 6,990,175 B2 | 1/2006 | Nakashima et al. |
| 7,020,233 B1 | 3/2006 | Tybinkowski et al. |
| 7,026,622 B2 | 4/2006 | Kojima et al. |
| 7,110,808 B2 | 9/2006 | Adair |
| 7,154,096 B2 | 12/2006 | Amano |
| 7,167,542 B2 | 1/2007 | Juschka et al. |
| 7,199,382 B2 | 4/2007 | Rigney et al. |
| 7,227,925 B1 | 6/2007 | Mansfield et al. |
| 7,242,750 B2 | 7/2007 | Tsujita |
| 7,263,165 B2 | 8/2007 | Ghelmansarai |
| 7,265,356 B2 | 9/2007 | Pelizzari et al. |
| 7,266,175 B1 | 9/2007 | Romesberg |
| 7,280,633 B2 | 10/2007 | Cheng et al. |
| 7,291,840 B2 | 11/2007 | Fritzler et al. |
| 7,297,958 B2 | 11/2007 | Kojima et al. |
| 7,298,821 B2 | 11/2007 | Ein-Gal |
| 7,310,410 B2 | 12/2007 | Sohal et al. |
| 7,386,099 B1 | 6/2008 | Kasper et al. |
| 7,397,901 B1 | 7/2008 | Johnsen |
| 7,397,902 B2 | 7/2008 | Seeber et al. |
| 7,453,983 B2 | 11/2008 | Schildkraut et al. |
| 7,453,984 B2 | 11/2008 | Chen et al. |
| 7,469,035 B2 | 12/2008 | Keall et al. |
| 7,555,103 B2 | 6/2009 | Johnsen |
| 7,558,378 B2 | 7/2009 | Juschka et al. |
| 7,560,698 B2 | 7/2009 | Rietzel |
| 7,564,951 B2 | 7/2009 | Hasegawa et al. |
| 7,596,209 B2 | 9/2009 | Perkins |
| 7,627,082 B2 | 12/2009 | Kojima et al. |
| 7,639,853 B2 | 12/2009 | Olivera et al. |
| 7,656,999 B2 | 2/2010 | Hui et al. |
| 7,715,606 B2 | 5/2010 | Jeung et al. |
| 7,742,575 B2 | 6/2010 | Bourne |
| 7,755,055 B2 | 7/2010 | Schilling |
| 7,755,057 B2 | 7/2010 | Kim |
| 7,778,691 B2 | 8/2010 | Zhang et al. |
| 7,792,252 B2 | 9/2010 | Bohn |
| 7,795,590 B2 | 9/2010 | Takahashi et al. |
| 7,839,972 B2 | 11/2010 | Ruchala et al. |
| 7,885,371 B2 | 2/2011 | Thibault et al. |
| 7,949,095 B2 | 5/2011 | Ning et al. |
| 7,957,507 B2 | 6/2011 | Cadman |
| 7,965,819 B2 | 6/2011 | Nagata |
| 7,983,380 B2 | 7/2011 | Guertin et al. |
| 8,017,915 B2 | 9/2011 | Mazin |
| 8,059,782 B2 | 11/2011 | Brown |
| 8,063,376 B2 | 11/2011 | Maniawski et al. |
| 8,116,427 B2 | 2/2012 | Kojima et al. |
| 8,139,713 B2 | 3/2012 | Janbakhsh |
| 8,139,714 B1 | 3/2012 | Sahadevan |
| 8,144,962 B2 | 3/2012 | Busch et al. |
| 8,148,695 B2 | 4/2012 | Takahashi et al. |
| 8,232,535 B2 | 7/2012 | Olivera et al. |
| 8,280,002 B2 | 10/2012 | Bani-Hashemi et al. |
| 8,295,906 B2 | 10/2012 | Saunders et al. |
| 8,304,738 B2 | 11/2012 | Gagnon et al. |
| 8,335,296 B2 | 12/2012 | Dehler et al. |
| 8,357,903 B2 | 1/2013 | Wang et al. |
| 8,384,049 B1 | 2/2013 | Broad |
| 8,406,844 B2 | 3/2013 | Ruchala et al. |
| 8,442,287 B2 | 5/2013 | Fordyce, II et al. |
| 8,447,387 B2 | 5/2013 | Xu et al. |
| 8,461,538 B2 | 6/2013 | Mazin |
| 8,461,539 B2 | 6/2013 | Yamaya et al. |
| 8,467,497 B2 | 6/2013 | Lu et al. |
| 8,483,803 B2 | 7/2013 | Partain et al. |
| 8,509,383 B2 | 8/2013 | Lu et al. |
| 8,536,547 B2 | 9/2013 | Maurer, Jr. et al. |
| 8,537,373 B2 | 9/2013 | Humphrey |
| 8,581,196 B2 | 11/2013 | Yamaya et al. |

(56) References Cited

U.S. PATENT DOCUMENTS

| | | | |
|---|---|---|---|
| 8,588,367 B2 | 11/2013 | Busch et al. |
| 8,617,422 B2 | 12/2013 | Koschan et al. |
| 8,641,592 B2 | 2/2014 | Yu |
| 8,664,610 B2 | 3/2014 | Chuang |
| 8,664,618 B2 | 3/2014 | Yao |
| 8,712,012 B2 | 4/2014 | O'Connor |
| 8,716,669 B2 | 5/2014 | Myaoka et al. |
| 8,745,789 B2 | 6/2014 | Saracen et al. |
| 8,748,825 B2 | 6/2014 | Mazin |
| 8,767,917 B2 | 7/2014 | Ruchala et al. |
| 9,205,281 B2 | 12/2015 | Mazin |
| 9,283,403 B2 | 3/2016 | Mazin et al. |
| 9,649,509 B2 | 5/2017 | Mazin et al. |
| 9,694,208 B2 | 7/2017 | Mazin et al. |
| 9,731,148 B2 | 8/2017 | Olivera et al. |
| 9,764,161 B2 | 9/2017 | Mazin et al. |
| 9,820,700 B2 | 11/2017 | Mazin |
| 9,956,428 B2 | 5/2018 | Kelly |
| 10,143,857 B2 | 12/2018 | Mazin et al. |
| 10,159,852 B2 | 12/2018 | Mazin et al. |
| 10,327,716 B2 | 6/2019 | Mazin |
| 10,617,890 B2 | 4/2020 | Mazin et al. |
| 10,688,320 B2 | 6/2020 | Voronenko et al. |
| 10,695,583 B2 | 6/2020 | Mazin et al. |
| 10,745,253 B2 | 8/2020 | Saracen et al. |
| 10,959,686 B2 | 3/2021 | Mazin |
| 11,033,757 B2 | 6/2021 | Voronenko et al. |
| 11,141,607 B2 | 10/2021 | Mazin et al. |
| 2002/0051513 A1 | 5/2002 | Pugachev et al. |
| 2002/0137991 A1 | 9/2002 | Scarantino et al. |
| 2002/0163994 A1 | 11/2002 | Jones |
| 2002/0191734 A1 | 12/2002 | Kohima et al. |
| 2002/0193685 A1 | 12/2002 | Mate et al. |
| 2003/0036700 A1 | 2/2003 | Weinberg |
| 2003/0128801 A1 | 7/2003 | Eisenberg et al. |
| 2003/0219098 A1 | 11/2003 | McNutt et al. |
| 2004/0024300 A1 | 2/2004 | Graf |
| 2004/0030246 A1 | 2/2004 | Townsend et al. |
| 2004/0057557 A1 | 3/2004 | Nafstadius |
| 2004/0158416 A1 | 8/2004 | Slates |
| 2006/0002511 A1 | 1/2006 | Miller et al. |
| 2006/0072699 A1 | 4/2006 | Mackie et al. |
| 2006/0113482 A1 | 6/2006 | Pelizzari et al. |
| 2006/0159220 A1 | 7/2006 | Heuscher |
| 2006/0173294 A1 | 8/2006 | Ein-Gal |
| 2006/0182326 A1 | 8/2006 | Schildkraut et al. |
| 2006/0193435 A1 | 8/2006 | Hara et al. |
| 2006/0237652 A1 | 10/2006 | Kimchy et al. |
| 2007/0003010 A1 | 1/2007 | Guertin et al. |
| 2007/0003123 A1 | 1/2007 | Fu et al. |
| 2007/0014391 A1 | 1/2007 | Mostafavi et al. |
| 2007/0025513 A1 | 2/2007 | Gheimansarai |
| 2007/0043289 A1 | 2/2007 | Adair |
| 2007/0053491 A1 | 3/2007 | Schildkraut et al. |
| 2007/0055144 A1 | 3/2007 | Neustadter et al. |
| 2007/0075273 A1 | 4/2007 | Birgy et al. |
| 2007/0085012 A1* | 4/2007 | Thompson ............ G01T 1/2985 250/363.05 |
| 2007/0211857 A1 | 9/2007 | Urano et al. |
| 2007/0221869 A1 | 9/2007 | Song |
| 2007/0242801 A1 | 10/2007 | Mackie et al. |
| 2007/0265528 A1 | 11/2007 | Xu et al. |
| 2008/0031404 A1 | 2/2008 | Khamene et al. |
| 2008/0071131 A1 | 3/2008 | Rietzel |
| 2008/0128631 A1 | 6/2008 | Suhami |
| 2008/0130825 A1 | 6/2008 | Fu et al. |
| 2008/0152085 A1 | 6/2008 | Saracen et al. |
| 2008/0156993 A1 | 7/2008 | Weinberg et al. |
| 2008/0205588 A1 | 8/2008 | Kim |
| 2008/0230705 A1 | 9/2008 | Rousso et al. |
| 2008/0253516 A1 | 10/2008 | Hui et al. |
| 2008/0273659 A1 | 11/2008 | Guertin et al. |
| 2008/0298536 A1 | 12/2008 | Ein-Gal |
| 2009/0003655 A1 | 1/2009 | Wollenweber |
| 2009/0086909 A1 | 4/2009 | Hui et al. |
| 2009/0116616 A1 | 5/2009 | Lu et al. |
| 2009/0169082 A1 | 7/2009 | Mizuta et al. |
| 2009/0256078 A1 | 10/2009 | Mazin |
| 2010/0040197 A1 | 2/2010 | Maniawski et al. |
| 2010/0054411 A1 | 3/2010 | Nord et al. |
| 2010/0054412 A1 | 3/2010 | Brinks et al. |
| 2010/0067660 A1 | 3/2010 | Maurer, Jr. et al. |
| 2010/0069742 A1 | 3/2010 | Partain et al. |
| 2010/0074400 A1 | 3/2010 | Sendai |
| 2010/0074408 A1 | 3/2010 | Bert et al. |
| 2010/0074498 A1 | 3/2010 | Breeding et al. |
| 2010/0086183 A1 | 4/2010 | Vik et al. |
| 2010/0150309 A1 | 6/2010 | Nord et al. |
| 2010/0166274 A1 | 7/2010 | Busch et al. |
| 2010/0176309 A1 | 7/2010 | Mackie et al. |
| 2011/0006212 A1 | 1/2011 | Shchory et al. |
| 2011/0044429 A1 | 2/2011 | Takahashi et al. |
| 2011/0073763 A1 | 3/2011 | Subbarao |
| 2011/0092814 A1 | 4/2011 | Yamaya et al. |
| 2011/0215248 A1* | 9/2011 | Lewellen ............... A61B 6/037 250/363.03 |
| 2011/0272600 A1 | 11/2011 | Bert et al. |
| 2011/0291015 A1 | 12/2011 | Mazin |
| 2011/0297833 A1 | 12/2011 | Takayama |
| 2011/0301449 A1 | 12/2011 | Maurer, Jr. |
| 2011/0309252 A1 | 12/2011 | Moriyasu et al. |
| 2011/0309255 A1 | 12/2011 | Bert et al. |
| 2011/0313231 A1 | 12/2011 | Guertin et al. |
| 2011/0313232 A1 | 12/2011 | Balakin |
| 2012/0230464 A1 | 9/2012 | Ling et al. |
| 2012/0292534 A1 | 11/2012 | Geneser et al. |
| 2013/0102830 A1 | 4/2013 | Otto |
| 2013/0188856 A1 | 7/2013 | Adler, Jr. et al. |
| 2013/0266116 A1 | 10/2013 | Abenaim et al. |
| 2014/0105355 A1 | 4/2014 | Toimela et al. |
| 2014/0107390 A1 | 4/2014 | Brown et al. |
| 2014/0163368 A1 | 6/2014 | Rousso et al. |
| 2014/0193336 A1 | 7/2014 | Rousso et al. |
| 2014/0217294 A1 | 8/2014 | Rothfuss et al. |
| 2014/0239204 A1 | 8/2014 | Orton et al. |
| 2014/0249348 A1* | 9/2014 | Mazin .................. G01T 1/2985 600/1 |
| 2015/0161338 A1 | 6/2015 | Scherrer et al. |
| 2015/0251017 A1 | 9/2015 | De Crevoisier et al. |
| 2015/0367143 A1 | 12/2015 | Muraki et al. |
| 2016/0023019 A1 | 1/2016 | Filiberti et al. |
| 2016/0331997 A1 | 11/2016 | Vilsmeier |
| 2016/0361566 A1 | 12/2016 | Larkin et al. |
| 2017/0014642 A1 | 1/2017 | An et al. |
| 2017/0028220 A1 | 2/2017 | Schulte et al. |
| 2017/0368372 A1 | 12/2017 | Mazin et al. |
| 2018/0001109 A1 | 1/2018 | Mazin et al. |
| 2018/0133518 A1 | 5/2018 | Harper et al. |
| 2018/0369611 A1 | 12/2018 | Owens et al. |
| 2019/0001152 A1 | 1/2019 | O'Connor et al. |
| 2019/0083815 A1 | 3/2019 | Mazin et al. |
| 2019/0091487 A1 | 3/2019 | Pal et al. |
| 2019/0255362 A1 | 8/2019 | Voronenko et al. |
| 2019/0357859 A1 | 11/2019 | Mazin |
| 2020/0222724 A1 | 7/2020 | Mazin et al. |
| 2021/0196212 A1 | 7/2021 | Mazin |
| 2021/0236854 A1 | 8/2021 | Voronenko et al. |
| 2022/0096867 A1 | 3/2022 | Mazin et al. |

FOREIGN PATENT DOCUMENTS

| | | |
|---|---|---|
| CN | 101496018 A | 7/2009 |
| CN | 101970043 A | 2/2011 |
| CN | 102068763 A | 5/2011 |
| CN | 102641561 A | 8/2012 |
| CN | 103845068 A | 6/2014 |
| CN | 104994909 A | 10/2015 |
| DE | 10 2008 053321 A1 | 5/2010 |
| EP | 2 188 815 B1 | 5/2010 |
| EP | 2 687 259 A1 | 1/2014 |
| JP | 09-33658 A | 2/1997 |
| JP | 9-189769 A2 | 7/1997 |
| JP | 2000-105279 A | 4/2000 |
| JP | 2001-340474 A | 12/2001 |

(56) References Cited

FOREIGN PATENT DOCUMENTS

| | | |
|---|---|---|
| JP | 2003-534823 A | 11/2003 |
| JP | 2004-513735 A | 5/2004 |
| JP | 2006-145281 A | 6/2006 |
| JP | 2007-502166 A | 2/2007 |
| JP | 2007-507246 A | 3/2007 |
| JP | 2008-173299 A | 7/2008 |
| JP | 2010-517655 A | 5/2010 |
| JP | 2011-514213 A | 5/2011 |
| JP | 2012-035072 A | 2/2012 |
| JP | 2014-023741 A | 2/2014 |
| JP | 2016-168077 A | 9/2016 |
| WO | WO-89/10090 A1 | 11/1989 |
| WO | WO-2000/015299 A1 | 3/2000 |
| WO | WO-2004/017832 A2 | 3/2004 |
| WO | WO-2004/017832 A3 | 3/2004 |
| WO | WO-2005/018734 A2 | 3/2005 |
| WO | WO-2005/018734 A3 | 3/2005 |
| WO | WO-2005/018735 A2 | 3/2005 |
| WO | WO-2005/018735 A3 | 3/2005 |
| WO | WO-2005/110495 A1 | 11/2005 |
| WO | WO-2007/045076 A1 | 4/2007 |
| WO | WO-2007/124760 A1 | 11/2007 |
| WO | WO-2008/019118 A2 | 2/2008 |
| WO | WO-2008/024463 A2 | 2/2008 |
| WO | WO-2008/024463 A3 | 2/2008 |
| WO | WO-2009/111580 A2 | 9/2009 |
| WO | WO-2009/111580 A3 | 9/2009 |
| WO | WO-2010/015358 A1 | 2/2010 |
| WO | WO-2010/110255 A1 | 9/2010 |
| WO | WO-2012/135771 A1 | 10/2012 |
| WO | WO-2013/093852 A1 | 6/2013 |
| WO | WO-2015/168431 A1 | 11/2015 |
| WO | WO-2018/183748 A1 | 10/2018 |

OTHER PUBLICATIONS

Banged, M. et al. (2016). "Accelerated iterative beam angle selection in IMRT," Medical Physics 43.3:1073-1082.
Chang, J.Y. et al. (2008). "Image-Guided Radiation Therapy for Non-Small Cell Lung Cancer," *J. Thorac. Oncol. FEB* 3(2):177-186.
Chen, X. et al. (2012). "Smoothing proximal gradient method for general structured sparse regression," The Annals of Applied Statistics 6:719-752.
Dieterich, S. et al. (2003). "Skin respiratory motion tracking for stereotactic radiosurgery using the CyberKnife," *Elsevier Int'l Congress Series* 1256:130-136.
Erdi, Y.E. (Feb. 2007). "The Use of PET for Radiotherapy," *Current Medical Imaging Reviews* 3(1):3-16.
Extended European Search Report dated Mar. 31, 2017, for European Application No. 09 719 473.2, filed on Mar. 9, 2009, 8 pages.
Extended European Search Report dated Oct. 7, 2015, for European Application No. 12 763 280.0, filed on Mar. 30, 2012, 11 pages.
Extended European Search Report dated Nov. 21, 2018, for European Application No. 18 168 947.2, filed on Mar. 30, 2012, 8 pages.
Extended European Search Report dated Oct. 15, 2019, for European Application No. 17 764 132.1, filed on Mar. 9, 2017, 4 pages.
Fan, Q. (Nov. 2012). "Emission Guided Radiation Therapy for Lung and Prostate Cancers: A Feasibility Study on a Digital Patient," *Med. Phys.* 39(11):7140-7152.
Fan, Q. et al. (Aug. 2013). "Toward a Planning Scheme for Emission Guided Radiation Therapy (EGRT): FDG Based Tumor Tracking in a Metastatic Breast Cancer Patient," *Med. Phys.* 40(8):081708, 12 pages.
Final Office Action dated Aug. 2, 2018, for U.S. Appl. No. 15/684,710, filed Aug. 23, 2017, 8 pages.
Fontenla, D.P. et al. (2008). "IMRT treatment plans: Dosimetry measurements & monitor units validation," Presentation Slides, 133 total pages.
Fredriksson (2013). "Robust optimization of radiation therapy accounting for geometric uncertainty," KTH Engin. Sciences, pp. 8-14.

Gibbons, J.P. (2004). "Dose calculation and verification for tomotherapy," 2004 ACMP Meeting, Scottsdale, AZ., 71 total pages.
Handsfield, L.L. et al. (2014). "Phantomless patient-specific TomoTherapy QA via delivery performance monitoring and a secondary Monte Carlo dose calculation," *Med. Phys.* 41:101703-1-101703-9.
International Search Report dated Jul. 20, 2012, for PCT Patent Application No. PCT/US2012/31704, filed on Mar. 30, 2012, 2 pages.
International Search Report dated Jun. 27, 2017, for PCT Patent Application No. PCT/US2017/021647, filed on Mar. 9, 2017, 3 pages.
International Search Report dated Jan. 17, 2018, for PCT Application No. PCT/US2017/061728, filed on Nov. 15, 2017, 2 pages.
International Search Report dated Oct. 3, 2018, for PCT Application No. PCT/US2018/035188, filed on May 30, 2018, 4 pages.
International Search Report dated Jun. 14, 2019, for PCT Application No. PCT/US2019/017855, filed on Feb. 13, 2019, 4 pages.
International Search Report dated Apr. 23, 2020, for PCT Application No. PCT/US2020/013927, filed on Jan. 16, 2020, 3 pages.
International Search Report dated Nov. 16, 2018, for PCT Application No. PCT/US2018/039104, filed on Jun. 22, 2018, 4 pages.
International Search Report dated May 4, 2009, for PCT Patent Application No. PCT/US2009/01500, filed on Mar. 9, 2009, 3 pages.
Kapatoes, J.M. et al. (2001). "A feasible method for clinical delivery verification and dose reconstruction in tomotherapy," *Med. Phys.* 28:528-542.
Kapatoes, J. M. (2001). "On the accuracy and effectiveness of dose reconstruction for tomotherapy," *Physics in Med. Biol.* 46:943-966.
Keall, P.J. et al. (2001). "Motion adaptive x-ray therapy: a feasibility study," *Physics in Med. Biol.* 46:1-10.
Krouglicof, N. et al. (Nov. 2013). "Development of a Novel PCB-Based Voice Coil Actuator for Opto-Mechatronic Applications," presented at *IEEE/RSJ International Conference on Intelligent Robots and Systems (IROS)*, Tokyo, Japan, Nov. 3-7, 2013, pp. 5834-5840.
Langen, K.M. et al. (2010). "QA for helical tomotherapy: Report of the AAPM task group 148," Med. Phys. 37:4817-4853.
Lee, S. et al. (2015). "Treatment plan comparison of Linac step and shoot, tomotherapy, RapidArc, and proton therapy for prostate cancer using dosimetrical and biological index," J. Korean Physical Society 67:7-16 (with tables 1-5), 28 total pages.
Lu, W. (2008). "Real-time motion-adaptive delivery (MAD) using binary MLC: I. Static beam (topotherapy) delivery," Phys. Med. Biol. 53:6491-6511.
Lu, W. (2009). "Real-time motion-adaptive-optimization (MAO) in tomotherapy," Phys. Med. Biol. 54:4373-4398.
Mackie, T.R. et al. (Nov.-Dec. 1993). "Tomotherapy: A New Concept for the Delivery of Dynamic Conformal Radiotherapy," *Med. Phys.* 20(6):1709-1719.
Manikandan et al. (2013). "Role of step size and max dwell time in anatomy based inverse optimization for prostate implants," J. Med. Phys. 38:148-154.
Mazin, S.R. et al. (Dec. 2010). "Emission-Guided Radiation Therapy: Biologic Targeting and Adaptive Treatment," *Journal of American College of Radiology* 7(12):989-990.
McMahon, R. et al. (2008). "A real-time dynamic-MLC control algorithm for delivering IMRT to targets undergoing 2D rigid motion in the beam's eye view," Med. Phys. 35:3875-3888.
Non-Final Office Action dated Feb. 24, 2017, for U.S. Appl. No. 15/069,390, filed Mar. 14, 2016, 6 pages.
Non-Final Office Action dated Feb. 21, 2018, for U.S. Appl. No. 15/684,710, filed Aug. 23, 2017, 10 pages.
Non-Final Office Action dated Mar. 27, 2018, for U.S. Appl. No. 15/684,693, filed Aug. 23, 2017, 7 pages.
Non-Final Office Action dated Aug. 30, 2019, for U.S. Appl. No. 16/193,725, filed Nov. 16, 2018, 5 pages.
Non-Final Office Action dated Sep. 19, 2019, for U.S. Appl. No. 16/217,417, filed Dec. 12, 2018, 7 pages.
Non-Final Office Action dated Jun. 26, 2020, for U.S. Appl. No. 16/122,735, filed Sep. 5, 2018, 16 pages.

(56) References Cited

OTHER PUBLICATIONS

Non-Final Office Action dated Dec. 6, 2019, for U.S. Appl. No. 15/993,325, filed May 30, 2018, 8 pages.
Notice of Allowance dated May 18, 2017, for U.S. Appl. No. 15/069,390, filed Mar. 14, 2016, 5 pages.
Notice of Allowance dated Jul. 19, 2017, for U.S. Appl. No. 15/499,671, filed Apr. 27, 2017, 8 pages.
Notice of Allowance dated Oct. 3, 2018, for U.S. Appl. No. 15/684,693, filed Aug. 23, 2017, 5 pages.
Notice of Allowance dated Oct. 25, 2018, for U.S. Appl. No. 15/684,710, filed Aug. 23, 2017, 7 pages.
Notice of Allowance dated Mar. 13, 2020, for U.S. Appl. No. 16/217,417, filed Dec. 12, 2018, 6 pages.
Notice of Allowance dated Apr. 20, 2020, for U.S. Appl. No. 15/993,325, filed May 30, 2018, 7 pages.
Olivera, G.H. et al. (2000). "Modifying a plan delivery without re-optimization to account for patient offset in tomotherapy," Proceedings of the 22$^{nd}$ Annual EMBS International Conference, Jul. 23-28, 2000, Chicago, IL, pp. 441-444.
Papanikolaou, N. et al. (2010). "MU-Tomo: Independent dose validation software for helical tomo therapy," *J. Cancer Sci. Ther.* 2:145-152.
Parodi, K. (2015). "Vision 20/20: Positron emission tomography in radiation therapy planning, delivery, and monitoring," Am. Assoc. Phys. Med. 42:7153-7168.
Prabhaker, R. et al. (2007, e-published Jan. 2008). "An Insight into PET-CT Based Radiotherapy Treatment Planning," *Cancer Therapy* (5):519-524.
Tashima, H. et al. (Jul. 21, 2012). "A Single-Ring OpenPET Enabling PET Imaging During Radiotherapy," *Phys. Med. Biol.* 57(14):4705-4718.
The Partial Supplementary European Search Report, dated Jun. 25, 2015 for European Application No. 12763280.0, filed on Mar. 30, 2012, 6 pages.
Written Opinion dated Jul. 20, 2012, for PCT Patent Application No. PCT/US2012/31704, filed on Mar. 30, 2012, 10 pages.

Written Opinion of the International Searching Authority dated Jun. 27, 2017, for PCT Patent Application No. PCT/US2017/021647, filed on Mar. 9, 2017, 5 pages.
Written Opinion of the International Searching Authority dated Jan. 17, 2018, for PCT Application No. PCT/US2017/061728, filed on Nov. 15, 2017, 7 pages.
Written Opinion of the International Searching Authority dated Oct. 3, 2018, for PCT Application No. PCT/US2018/035188, filed on May 30, 2018, 28 pages.
Written Opinion of the International Searching Authority dated Jun. 14, 2019, for PCT Application No. PCT/US2019/017855, filed on Feb. 13, 2019, 10 pages.
Written Opinion of the International Searching Authority dated Apr. 23, 2020, for PCT Application No. PCT/US2020/013927, filed on Jan. 16, 2020, 4 pages.
Written Opinion of the International Searching Authority dated Nov. 16, 2018, for PCT Application No. PCT/US2018/039104, filed on Jun. 22, 2018, 6 pages.
Written Opinion dated May 4, 2009, for PCT Patent Application No. PCT/US2009/01500, filed on Mar. 9, 2009, 5 pages.
Yamaya, T. et al. (Jan. 14, 2008). "A Proposal of an Open PET Geometry," *Physics in Medicine and Biology* 53:757-773.
Yan, D. et al. (1997). "Adaptive radiation therapy," *Physics Med. Biol.* 42:123-132.
Corrected Notice of Allowability dated Feb. 3, 2021, for U.S. Appl. No. 16/425,416, filed May 29, 2019, 2 pages.
Non-Final Office Action dated Oct. 29, 2020. for U.S. Appl. No. 16/834,956, filed Mar. 30, 2020, 7 pages.
Non-Final Office Action dated Dec. 22, 2020, for U.S. Appl. No. 16/554,258, filed Aug. 28, 2019, 11 pages.
Notice of Allowance dated Jan. 21, 2020, for U.S. Appl. No. 16/193,725, filed Nov. 16, 2018, 7 pages.
Thorwarth, D. et al. (2010). "Physical radiotherapy treatment planning based on functional PET/CT data," Radiotherapy Oncology, pp. 317-324.

\* cited by examiner

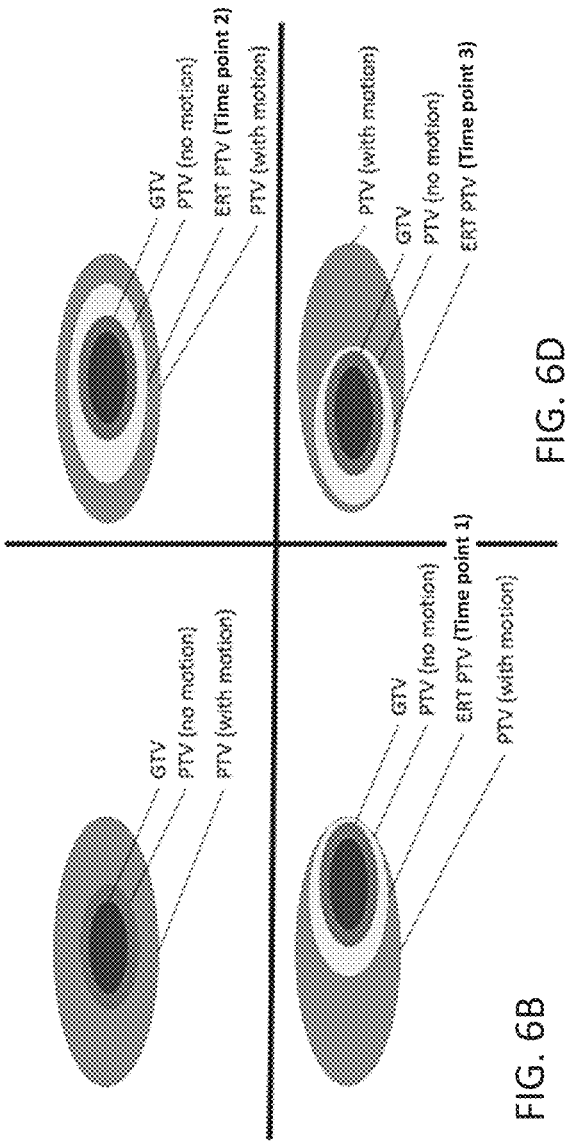

METHODS FOR RADIATION DELIVERY IN EMISSION-GUIDED RADIOTHERAPY

CROSS-REFERENCE TO RELATED APPLICATIONS

This application is a continuation application of International Application No. PCT/US2017/061728, filed Nov. 15, 2017, which claims priority to U.S. Provisional Application Ser. No. 62/422,276, filed Nov. 15, 2016, the disclosures of which are hereby incorporated by reference in their entireties.

TECHNICAL FIELD

This application relates to methods for delivering radiation to a positron-emitting target region under continuous PET guidance. The methods generally include detecting a pattern of positron emission lines-of-response (LORs) that intersect the target. In response to the pattern, radiation may be delivered along paths that are not necessarily collinear to any of the LORs. Methods for further modifying radiation delivery, as well as the detected LOR population, are also described.

BACKGROUND

Positron emission tomography (PET) is a medical imaging modality that is frequently used to detect cancerous tissue in the body. A molecule labeled with a radioactive atom, known as a PET radiotracer, is first injected into the patient. The radioactive atoms inside the patient undergo radioactive decay and emit positrons. Once emitted from an atom, a positron will quickly collide with a nearby electron after which both will be annihilated. Two high energy photons (511 keV) are emitted from the point of annihilation and travel in opposite directions. When the two photons are simultaneously detected by two PET detectors, it is known that the annihilation occurred somewhere along the line joining the two PET detectors. This line is called a positron emission path or line-of-response (LOR). The information collected from millions of these emission paths is used to gradually assemble an image of the PET radiotracer distribution in the body.

Emission-Guided Radiotherapy (EGRT) generally uses these lines-of-response (LORs) originating from positron emission events in a target volume, e.g., a target tumor, to direct beamlets of therapeutic radiation to the target volume. EGRT may be performed using various types of radiation delivery systems, e.g., systems consisting of a linear accelerator (LINAC) and positron emission tomography (PET) detectors on a fast rotating closed ring gantry. During treatment of cancer patients with this type of system, the PET detectors collect LORs from tumor uptake sites and the LINAC responds in nearly real-time with beamlets of radiation along the same LOR paths. This ability to steer therapy in real-time based on a signal coming directly from the tumor enables a more precise delivery of radiation.

Additionally, this type of direct biological targeting simplifies treatment planning for multiple targets (metastatic disease). However, accurate tumor tracking and radiation delivery, especially to account for target motion, still remain a challenge. Accordingly, improved methods for delivering radiation therapy with higher targeting accuracy would be useful to reduce radiation exposure to surrounding non-target tissue.

SUMMARY

Described herein are methods for delivering radiation to a target region, such as a target volume within a subject for treating various types of tumors and other target tissues or organs. The disclosed methods generally aim to provide more efficient delivery of radiation by refining, tailoring, or customizing the delivery of radiation beam response paths in response to detected emission paths. For example, the methods may include determining which beamlets are delivered as part of the radiation response, as well as steps for modifying the radiation response and detected LOR population.

Current EGRT treatment delivery schemes typically rely on directing radiation at a collinear path along each detected LOR. In contrast, an alternative scheme is described herein that detects a plurality or population of LORs intersecting the target volume in a certain pattern, and in response to this pattern the radiation is delivered along paths that are not necessarily collinear to any of the LORs. That is, radiation is delivered along paths calculated from the pattern information (e.g., based on a reprojection of the plurality of LORs) instead of along emission paths.

In general, the methods described herein for delivering radiation to a subject include the steps of detecting a population of positron emission paths; detecting a pattern of positron emission paths within the population; determining one or more response paths based at least in part on processing of the pattern; and delivering radiation along the one or more response paths to a target volume within the subject.

The methods may further include such steps as filtering the population of positron emission paths, recording a dose of radiation delivered along the one or more response paths, and/or recording one or more undelivered response paths, where the undelivered response paths have a negative weight, and adding the negative weight to the weight of subsequently determined response paths.

The delivery of radiation may be repeated until a predetermined dose of radiation is received by the target volume. Additionally, the methods for delivering radiation may include tracking the breathing motion of the subject to account for target volume movement during the subject's breathing cycle. Furthermore, the methods may be used alone or in conjunction with surgery, chemotherapy, radiosensitizers, and/or brachytherapy for the treatment of tumors.

The methods for radiation delivery may be performed by an EGRT system comprising a circular gantry; a radiation source mounted on the gantry; a plurality of positron emission detectors mounted on the gantry, where the positron emission detectors detect the population of positron emission paths; and a controller in communication with the radiation source and the positron emission detectors. The radiation source may be positioned by rotating the gantry. A user interface may also be provided with the system for manually setting various controller and processing parameters, e.g., time window intervals for LOR detection, LOR pattern selection, employment of filtering, etc., by a user.

BRIEF DESCRIPTION OF THE DRAWINGS

FIG. 6A is a conceptual depiction of the increase in planned tumor volume (PTV) size with respiration in relation to the gross tumor volume (GTV) size.

FIG. 6B is a conceptual depiction of gross tumor volume (GTV) and estimated real-time planned tumor volume (ERT PTV) positions at a first time point in a breathing cycle.

FIG. 6C is a conceptual depiction of gross tumor volume (GTV) and estimated real-time planned tumor volume (ERT PTV) positions at a second time point in a breathing cycle.

FIG. 6D is a conceptual depiction of gross tumor volume (GTV) and estimated real-time planned tumor volume (ERT PTV) positions at a third time point in a breathing cycle

DETAILED DESCRIPTION

Figure 1A:
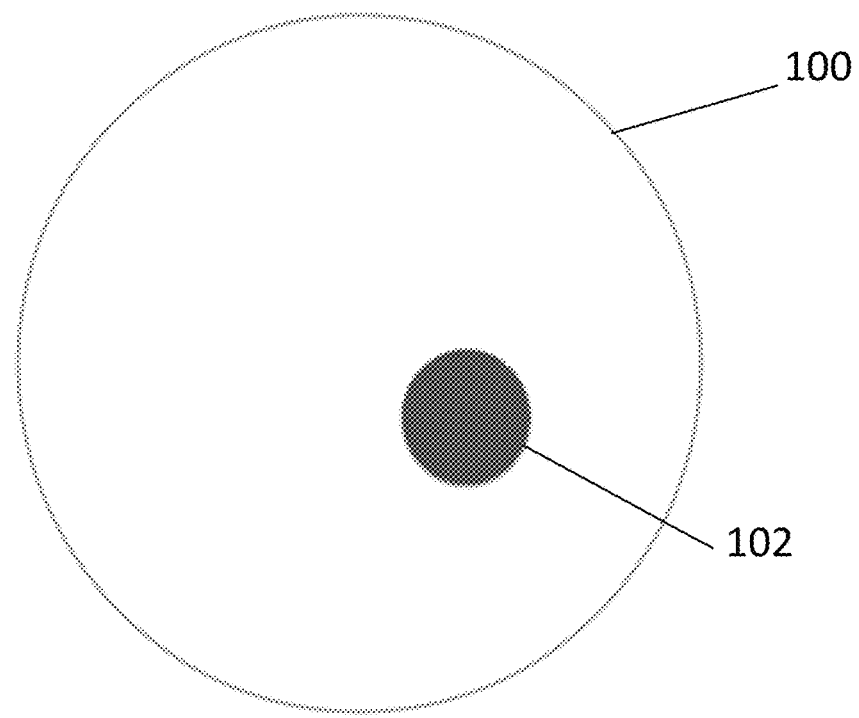
FIG. 1A is a conceptual depiction of a target volume within the circular gantry of an EGRT system.

Described herein are methods for delivering radiation to a target volume. These methods may be used for treating various types of tumors and other target tissues or organs. The disclosed methods generally aim to provide more efficient delivery of radiation by refining, tailoring, or customizing the delivery of radiation beam response paths in response to detected emission paths (detected LORs) so that they are not necessarily collinear to the LORs. Specifically, the delivery of radiation beam response paths can be calculated based upon a pattern of detected LORs. Processing of the LORs, either before or after detection of the pattern, can be employed to more precisely deliver radiation to the target volume, as further described below.

Subjects undergoing EGRT are typically administered a radiotracer, which is a source of positrons taken up by the target volume for subsequent detection. A typical radiotracer includes unstable nuclides that emit positrons. The positron has the same mass as an orbital electron but is positively charged. A unique characteristic of the positron is that it cannot exist at rest in nature. Once it loses its kinetic energy, the positron immediately combines with a negatively charged electron and undergoes an annihilation reaction in which the masses of the two particles are completely converted into energy in the form of two 511 KeV annihilation photons, which leave their production site at approximately 180 degrees from each other. The detection of the two 511 keV gamma rays forms the basis for targeting living tumor tissue with radiotracers.

A commonly used radiotracer in clinical practice and the study of cancers is fluorine-18 fluorodeoxyglucose (FDG), a metabolic PET radiotracer. FDG, a glucose analog, is taken up by high-glucose-using cells such as brain, kidney, and cancer cells, where phosphorylation prevents the glucose from being released intact. Thus, living diseased tissue will take up, and concentrate metabolic PET radiotracers more intensely than healthy tissue. It is understood that other radiotracers comprising positron-emitting radionuclides can be used, including but not limited to, Fluorine-18, Carbon-11, Oxygen-15, and Nitrogen-13. Other useful radiotracers include, but are not limited to, 18F-NaF, 18FHX4, 18FFAZA, 18FFMISO, radiolabeled 5F7 anti-HER2 nanobody labeled with 18F, 11C-Palmitate and 14-(R,S)-18F-fluoro-6-thiaheptadecanoic acid, 15O-Water, 13N-Ammonia, 82Rb-Rubidium, 18F-flurorothymidine, 68Ga-Gallium, 68Ge-Germanium, F18-Fluciclovine, Ga68-DOTATATE, C11-Choline, Ga68-PSMA, F18-PyL(PSMA), PD-L1, 13N-nitrogen, 11C-methionine, 18F-fluoroerythronitroimidazole, 3'-Aza-2'-[18F]fluorofolic acid, N-succinimidyl 3-((4-(4-(18)F-fluorobutyl)-1H-1,2,3-triazol-1-yl)methyl)-5-(guanidinomethyl)benzoate radiolabeled 5F7 antibody, 1-(2'-deoxy-2'-[18F]fluoroarabinofuranosyl) cytosine (18F-FAC), and F18-Fluciclovine. In some variations, the radiotracer may comprise a HER2 PET tracer such as 5F7 Anti-HER2 nanobody labeled with 18F (18F-RL-I-5F7) and 18F-SFB. In other variations, the radiotracer may comprise 18F-fluoromisonidazole (e.g., FMISO, FETNIM) and/or a 18F-fluoroazomycinarabinoside tracer (e.g., FETNIM). In yet further variations, the radiotracer may comprise (S)-4-(3-[18F]Fluoropropyl)-L-glutamic acid (18F-FSPG), [(18)F] DCFPyL (18F-PSMA), or Ga68-PSMA.

Figure 1B:
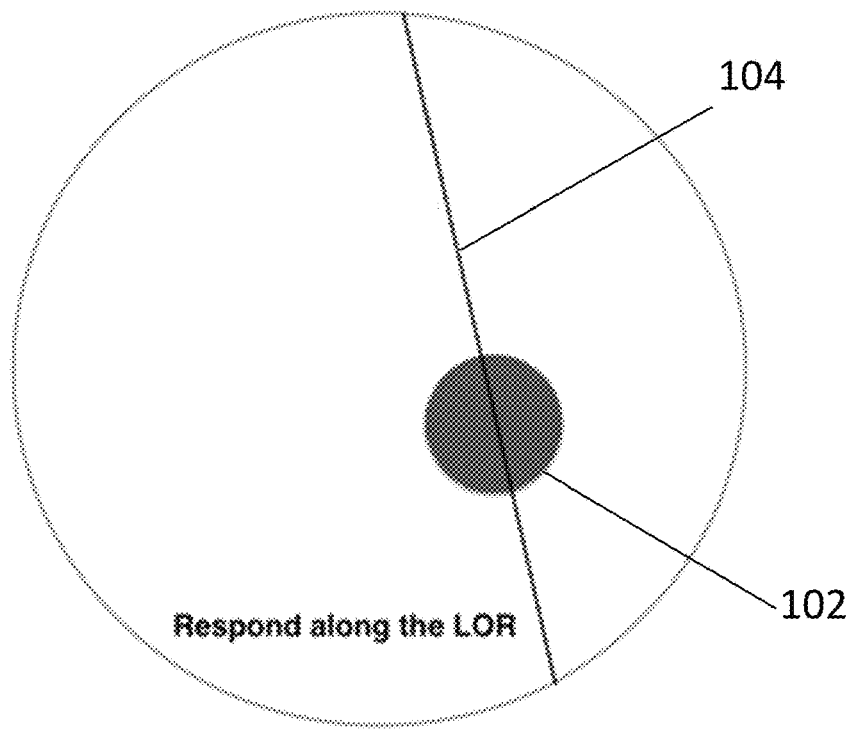
FIG. 1B is a conceptual depiction of radiation being delivered through the target volume shown in FIG. 1A along the same path as the positron emission line-of-response (LOR).

Exemplary systems that can be used for EGRT may comprise a circular gantry rotatable about a subject or a body area of the subject, one or more positron emission detectors coupled to the gantry, and one or more therapeutic radiation sources coupled to the gantry. The therapeutic radiation sources can deliver beamlets of radiation in response to emission paths from a target volume that are detected by the positron emission detectors. To illustrate, FIG. 1A shows a treatment bore (100) representative of a circular gantry that is rotatable about a target volume (102) within a subject or a body portion thereof. The target volume can include a tumor, a cancer, a body tissue or organ, etc. Upon detection of an emission path, i.e., a line-of-response (LOR), the gantry can be rotated based on commands generated by a controller, to align the therapeutic radiation source with the LOR and then deliver radiation along (i.e., collinear with) the LOR. For example, as shown in FIG. 1B, radiation is delivered along the same path as the detected LOR (104). In some variations, the gantry may be continuously rotating and delivering radiation based on a detected LOR.

A user interface may also be provided with the systems for manually setting various controller and processing parameters, e.g., time window intervals for LOR detection, LOR pattern selection, employment of filtering, etc., by a user.

EGRT Based on Pattern Detection

Alternatively, methods for EGRT using gantry-type systems as described herein may deliver beamlets of radiation that are not necessarily collinear with any detected LOR, but instead are based upon a detected pattern of LORs. These methods for delivering radiation to a subject may include the steps of detecting a population of positron emission paths (LORs); detecting a pattern of positron emission paths (LORs) within the population; determining one or more response paths based at least in part on processing of the pattern; and delivering radiation along the one or more response paths to a target volume within the subject. The pattern may comprise any suitable number of LORs (nLORs), but will typically comprise a smaller number of LORs in comparison to the number of LORs acquired to generate a PET image. For example, instead of collecting information from the millions of LORs needed to create a PET image, only about two (2) to a few thousand will be generally used in the LOR patterns described herein. The number of LORs in the pattern may range from about two (2) to about five (5) at the lower end to about 2,000-5,000 at the upper end. Furthermore, selection of the LOR pattern for processing can be based upon predefined criteria. The predefined criteria can be input from a user interface, and can vary depending on, e.g., the size, location, etc., of the target volume. In general, each time radiation is to be delivered, a population of LORs is detected within a designated time window and analyzed for patterns. When a pattern that meets predefined criteria is detected, a radiation response path is calculated and delivered from a particular gantry angle(s) or time interval(s).

Prior to a radiation session, a volume of interest is generally provided with a radiotracer, e.g., FDG. The radiotracer provides a source of positrons for real-time tracking of the target volume. Thereafter, a population of LORs can be detected and a pattern of LORs within the population detected. Next, one or more radiation response paths can be calculated based in part on processing of the pattern, and radiation delivered along one or more of the calculated response paths to a target volume (e.g., lesions or tumors within the subject).

While the methods for EGRT described herein may be configured to detect and respond to emission paths arising from PET tracers, other types of radioactive tracers may also be used for EGRT. For example, EGRT systems and methods may additionally or alternatively be configured to detect and respond to single photon emissions arising from SPECT tracers. Other radioactive tracers that are commonly used in nuclear medicine may also be used with the EGRT methods described herein. Emission rays from such radioactive tracers may serve as guidance for accurate and near real-time tumor tracking. Depending on the on type of radioactive tracer that is used, EGRT systems may comprise a variety of detectors, such as positron emission detectors, single-photon emission detectors, and the like. EGRT systems may also comprise a variety of therapeutic radiation sources, including linear accelerators, radioactive materials, x-ray sources, particle beam sources, etc.

In various situations, the location data is generated during a pre-treatment planning stage. In some situations, substantial imaging has been done to diagnose and track a volume of interest such as an area of diseased tissue. This imaging can be used to establish probable volumes within which target volumes or tumors of interest exist and move. The data may be generated from imaging completed during diagnosis. In some variations, location data of more than one volume is received such that radiation may be directed to several volumes during a treatment session. Identifying target volumes of interest, such as cancerous tumor tissue, for example, may include a number of modalities including, but not limited to, X-Ray imaging, Computed Tomography (CT), Magnetic Resonance Imaging (MM), Positron Emission Tomography (PET) or combinations thereof. Other imaging modalities are possible.

In some variations of the method, receiving the location data of the volume includes registering the volume with a reference point of the machine, such as the radiation source, for example. Registering the volume with the machine can include performing a low dose CT scan using the machine's radiation source. In other variations, receiving location data of one or more volumes and registering each volume with the machine includes detecting a number of emission events and mapping the events to identify the volumes. It is understood that other methods of registering a volume with the external radiation machine are possible. In further variations, receiving location data of the volumes includes receiving location data of areas not to irradiate.

Upon directing radiation toward a target volume, the amount or dose of radiation can be recorded. X-ray detectors located opposite the radiation source(s) can be used to record the radiation directed toward and passing through the target volume. For example, a controller can monitor the accumulated radiation and continue to detect patterns of LORs and direct radiation along calculated response paths until a prescribed dosage of radiation has been directed to each volume of interest. In addition, an ion chamber located on the same side as the radiation source and disposed between the linear accelerator and collimator can be used to record the delivered dose.

Figure 2:
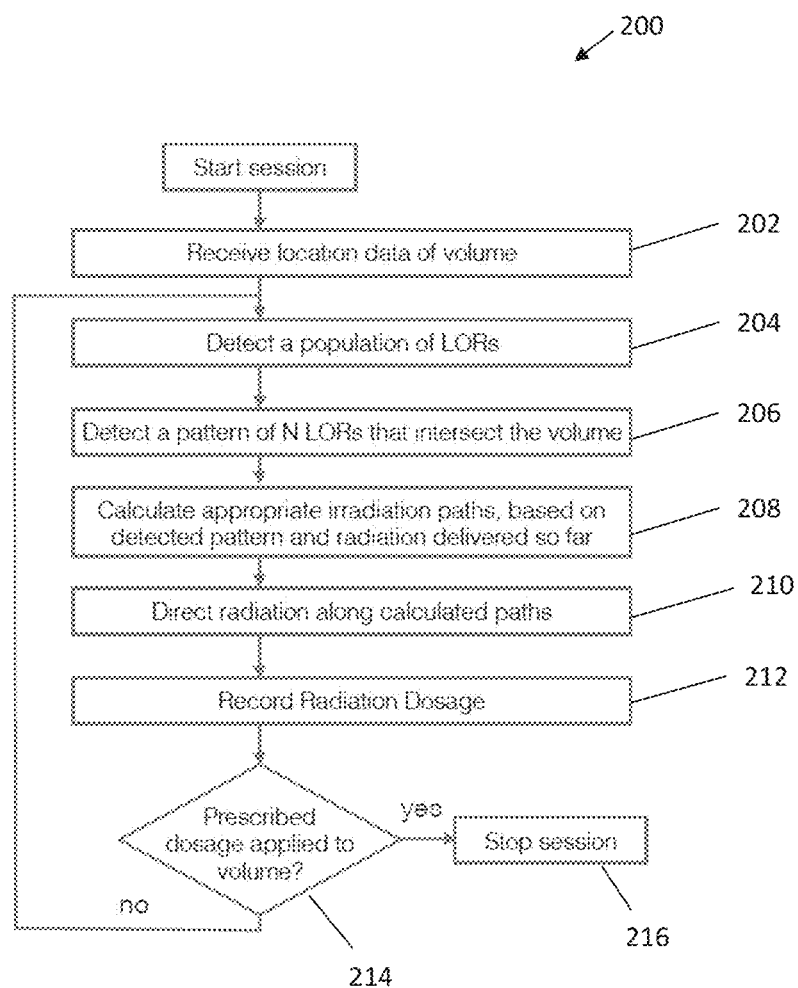
FIG. 2 is a flowchart illustrating an exemplary method for delivering radiation based upon detection and processing of a pattern of LORs.

In one variation, as illustrated by the flowchart in FIG. 2, the method of delivering radiation to a subject (200) can include the steps of receiving location data describing one or more volumes of interest (202). The method (200) further includes detecting a population of positron emission paths or LORs (204), detecting a pattern of LORs within the population that intersect the target volume (206), calculating or determining one or more appropriate response (irradiation) paths based at least in part on processing of the pattern (208); and delivering or directing radiation along the one or more calculated response paths to a target volume within the subject (210). The radiation dosage delivered to the target volume is recorded (212), e.g., by a controller, and a prescribed dosage determined (214). If the prescribed dosage has been met, then the treatment session is terminated (216). However, if the prescribed dosage has not been met, then the treatment session is continued and steps (204), (206), (208), (210), (212), and (214) are repeated. It is understood that one or more steps can be repeated in order to obtain the prescribed dosage.

Figure 3A:
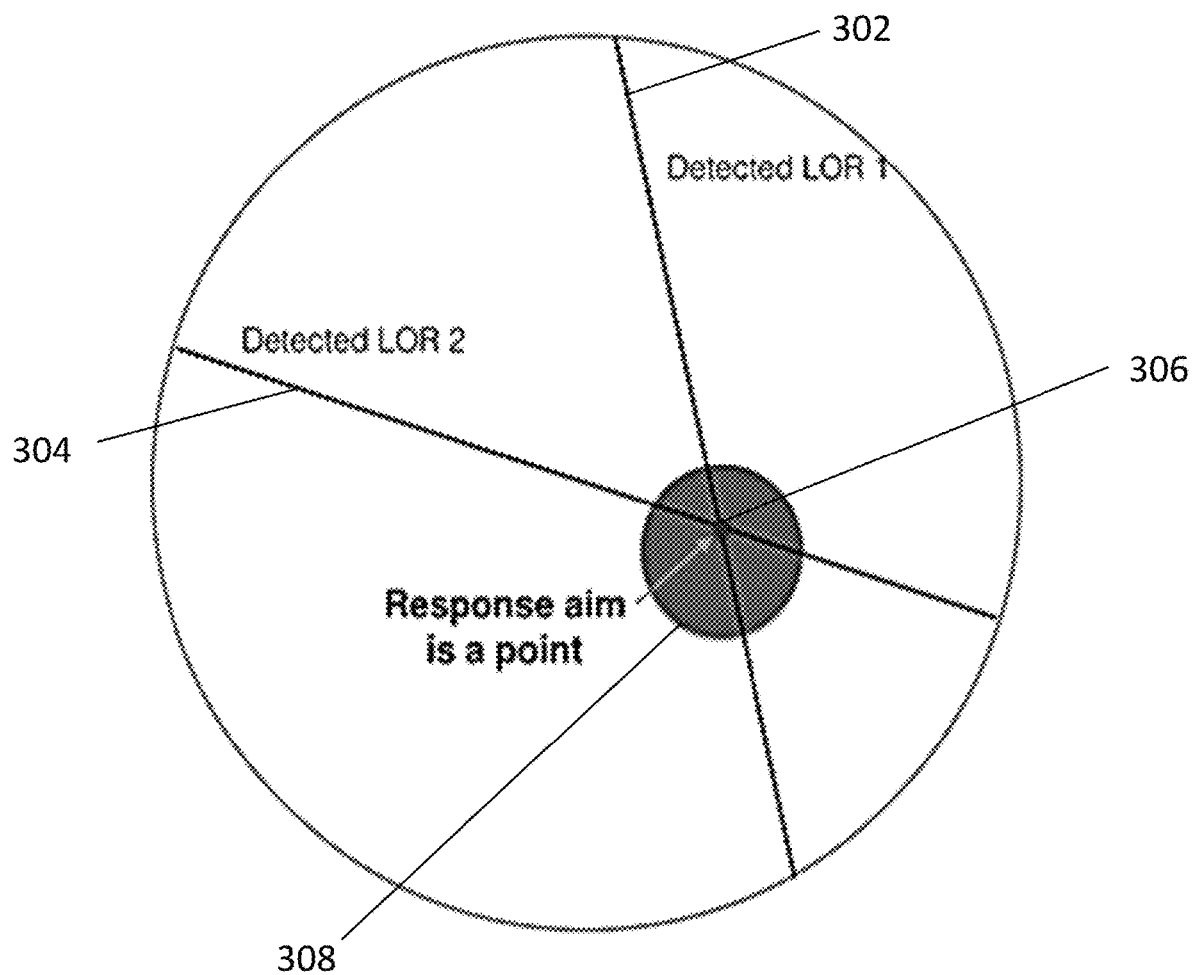
FIGS. 3A-3C are conceptual depictions of exemplary LOR patterns.
Figure 3B:
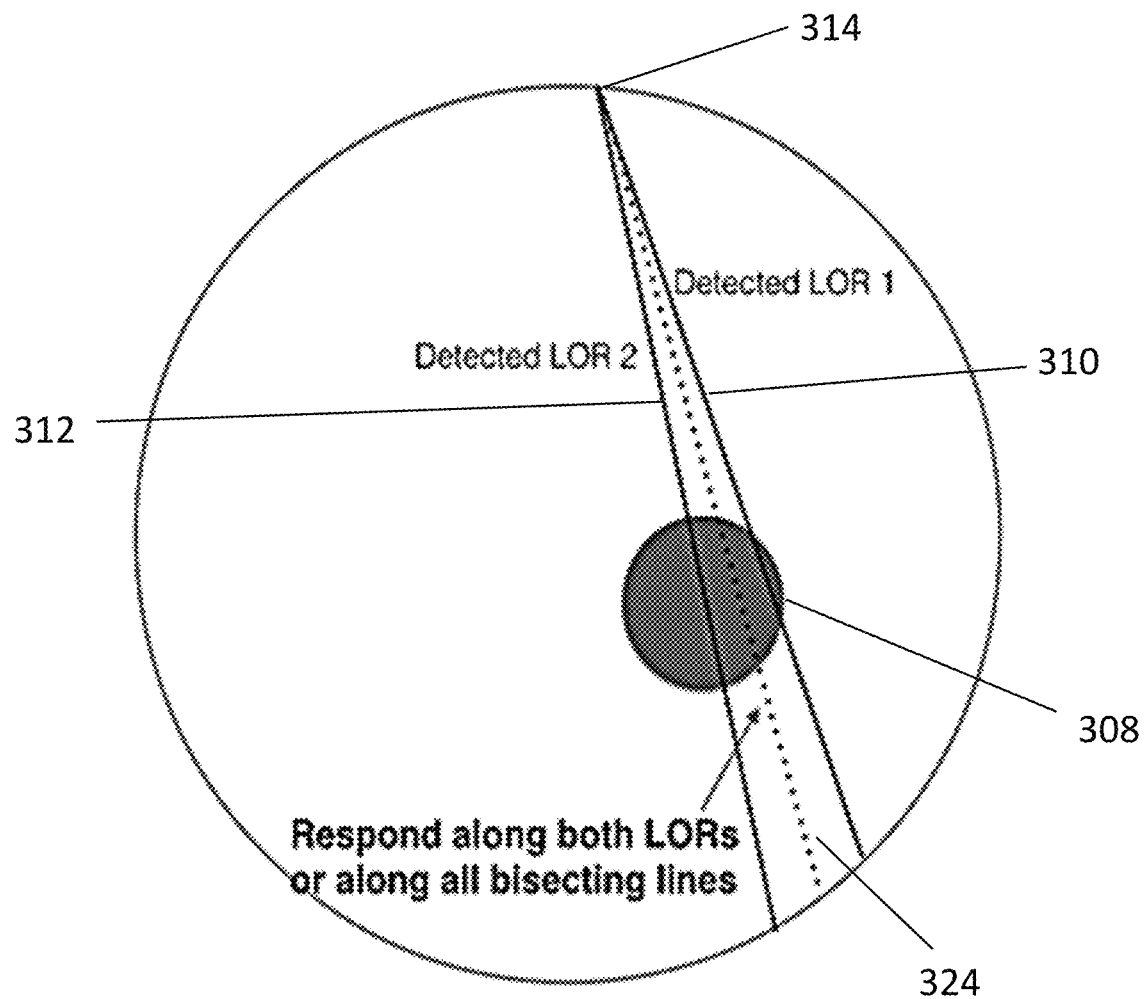
Figure 3C:
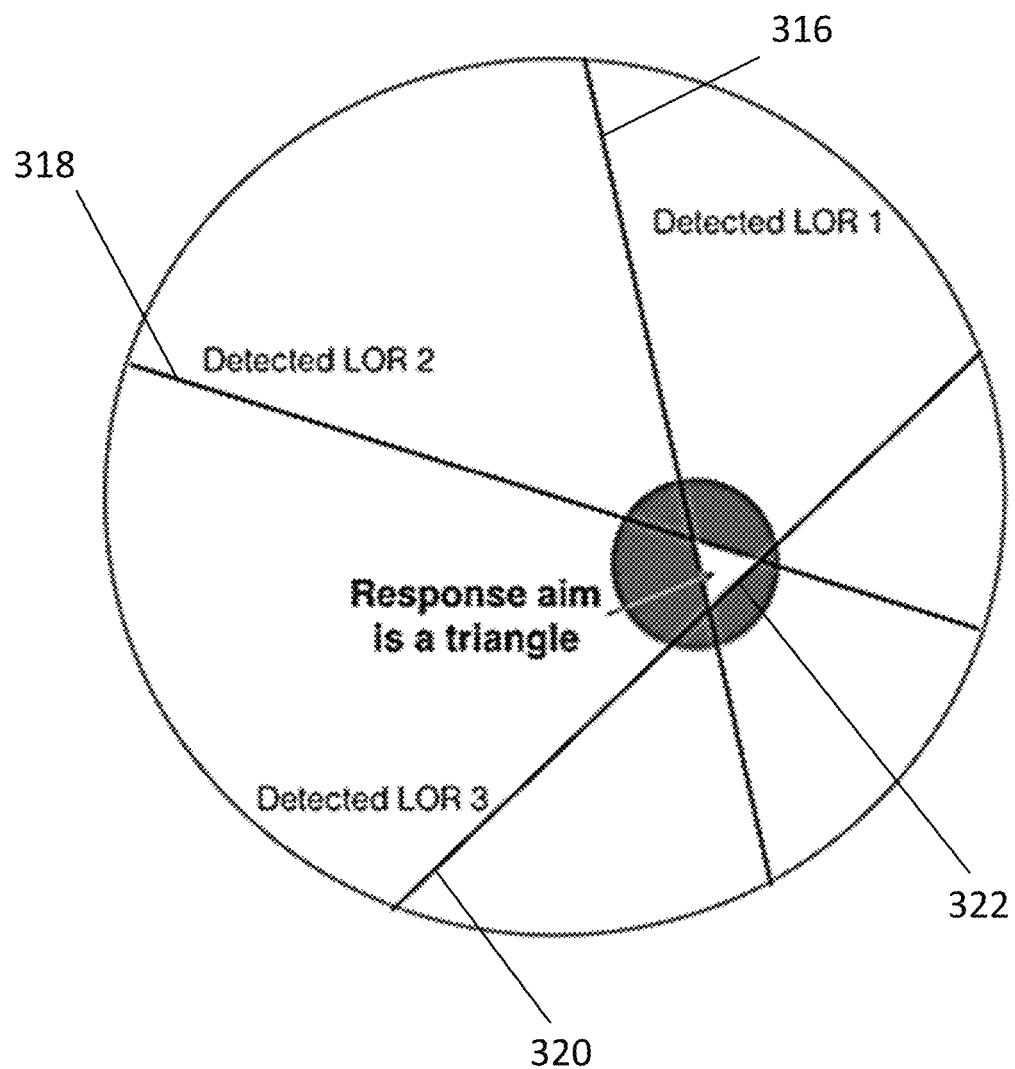

Various patterns from the detected population of LORs can be identified, and processing of the pattern implemented by a controller, computer, or other suitable processing hardware to calculate one or more paths for radiation delivery to a target volume. The detected LOR pattern will typically include a smaller number of LORs than that acquired to create a PET image, as previously stated. In some variations, the pattern may comprise positron emission paths that intersect at a point within the target volume. For example, as shown in FIG. 3A, the pattern can include two intersecting LORs (302, 304), where the intersection is at a point (306) within the target volume (308). In other variations, the pattern may comprise LORs that both intersect the target volume and intersect at (or near) the same firing position. For example, as shown in FIG. 3B, the pattern comprises two LORs (310, 312) that intersect the target volume (308) and intersect at the same firing position on the gantry (314). In yet further variations, the pattern may comprise LORs that intersect within the target volume to define a target area within the target volume. For example, as shown in FIG. 3C, the pattern comprises three LORs (316, 318, 320) that intersect to form target area, triangle (322) within target volume (308). It is understood that other patterns can be detected and used to calculate or determine radiation beam response paths. Other patterns may include without limitation, patterns comprising an arbitrary set of LORs that intersect the target volume. The arbitrary set of LORs will generally also include a smaller number of LORs than that acquired to create a PET image, at most on the order of thousands instead of millions. Alternatively, the pattern may comprise non-intersecting LORs.

The pattern that is detected can be processed to calculate one or more paths for radiation delivery to a target volume. In some variations, the radiation response includes paths that are both collinear and non-collinear to detected LORs in the pattern. For example, the radiation response may include at least two response paths that are collinear with a LOR from the detected pattern, or one or more response paths that are not collinear to any LOR from the detected pattern.

The calculations can be based on one or more detected LORs in the pattern. For example, in some variations, and as depicted in FIG. 3A, the radiation response can include multiple radiation beamlets (not shown) from a range of gantry angles that are aimed at LOR intersection point (306) within target volume (308). In other variations, and as depicted in FIG. 3B, multiple radiation beamlets (not shown) can be delivered in a manner that spans an angular extent of the detected LORs. Here the radiation can be delivered along detected LORs and/or one or more path lines therebetween (bisecting lines, 324). Alternatively, as provided in FIG. 3C, multiple beamlets (not shown) from a range of gantry angles can be delivered to cover a region within a target volume, such as triangle (322). In yet further variations, an entire population of LORs within a time window can be treated as a pattern, and a set of response paths calculated from the population.

During processing of the pattern, a weight can be assigned to the one or more response paths as part of the calculations, where the weight correlates to a radiation dose delivered along the one or more response paths. In some instances, the assigned weight has a negative value. In other instances, processing of the pattern can include calculating the weight of a set of response paths, the weight being proportional to the number of positron emission paths in the detected pattern. For example, when two LORs are received, the number of generated response paths should generally also be two, in order to respond to every LOR. Extending this concept to patterns, the total response path weight should generally be proportional to the number of LORs in the pattern. However, when filtering is used, e.g., when a sharpening or high-pass filter having a negative coefficient is used, the filter may modify the response weights such that they become negative.

Processing of the pattern can also include calculating a set of weighted response paths via a reprojection procedure. It may be useful in some variations, e.g., in response to an arbitrary LOR configuration, to reproject all LORs that intersect a target volume into an image space and direct radiation toward the resulting image. Here the entire LOR set is reprojected into an image space, which would yield a probability map of the LOR origination voxels. This probability map can be thresholded (yielding a binary mask) or used as is to form a set of radiation response paths. If a binary mask is obtained, the radiation can be directed at voxels having a value of 1. If a probability map is used as is, then a probabilistic leaf-by-leaf response can be used, using the voxel probability values as leaf opening probabilities. Additional details relating to reprojection are further described below with respect to filtering of the LORs.

Filtered EGRT Delivery

The methods for delivering radiation to a subject may also include filtering the population of detected emission paths (LORs). Filtering may be useful in improving the target radiation dose conformality, and/or to improve homogeneity of the delivered dose, and/or to improve other metrics relevant for radiation treatments. Filtering may also be useful when the general pattern comprises an arbitrary set of LORs that intersect the target volume. The filtering of LORs generally modifies the radiation response and the resulting delivered dose distribution. Filtering parameters can be based on predetermined or fixed criteria that are part of the algorithm run by the processing software, e.g., a ramp filter such as a finite impulse response (FIR) filter can be used to correct or remove peaks in the resulting image or dose distribution, as further described below. Alternatively, filtering can be accomplished by high-pass filters that filter out the background.

In some variations, a filter is applied to modify the incoming LOR sequence (LOR population), and the modified (filtered) LOR sequence is then used for making the radiation response determination. Generally, the filter can be implemented and characterized in a sinogram space, although other implementations are possible. When a sinogram space is employed, processing of the pattern can first include binning the population of LORs into a sinogram matrix. For example, LOR sequences may comprise binning them into a 3D sinogram matrix, or series of 2D sinogram matrices, called slices. In the simplest case, each LOR contributes a value of 1 into a single unique sinogram matrix entry value or "bin." Alternatively, in order to account for non-uniform PET detector sensitivity, the matrix can be organized so that some LORs will contribute only fractional values, e.g., a value less than 1, to their corresponding bins. For example, in some variations the PET detectors can be calibrated to have a higher LOR detection sensitivity (lower detection threshold) or a lower LOR detection sensitivity (higher detection threshold). Thus, when a highly sensitive detector is employed, the matrix value can be modified by assigning a weight or correction factor to the LOR to account for the detector's higher sensitivity. For example, a LOR detected at a highly sensitive detector may be assigned a weight of 0.7 instead 1 to account for the detector's lower detection threshold.

Overall, a sinogram matrix can be used to organize the detected population of LORs prior to filtering, which then modifies the values in the sinogram. The sinogram matrix can be organized as follows: matrix rows correspond to different LOR angles (i.e., a LOR angle is the gantry angle at which a LOR was detected), matrix columns correspond to different in-plane LOR distances from isocenter (i.e., gantry isocenter), and matrix slices correspond to different cross-plane distances (or distances from central imaging plane), which are taken along the axis perpendicular to the gantry.

Filtering can be applied to the organized sinogram matrix to improve the target radiation dose conformality, and/or to improve homogeneity of the delivered dose, and/or to improve other metrics relevant for radiation treatments, as previously stated. In some variations, a subset of incoming LORs is selected (e.g., the latest LORs within a certain time window). The subset is binned into a parallel-beam geometry or a fan-beam geometry sinogram matrix. For example, in the case of parallel-beam binning, P discrete distance bins are selected (ranging between 0 to PET field-of-view radius), and A angle bins are selected between 0 and 180 degrees, and Z cross-planes are selected (where Z typically=# of pet scanner rings). Here a sinogram is a (P×A×Z) matrix, where each (p, a, z) denotes the number of LORs detected with an angle within the bin 'a', and in-plane distance from isocenter within the bin 'p', and cross-plane distance within bin 'z'. The binning process just performs the counting, and results in a non-negative integer sinogram matrix. When PET scanner sensitivity is incorporated into the binning process, the sinogram matrix may also have non-negative real values.

Upon filtering of the sinogram matrix it is modified to generally result in a real-valued ("real") matrix, i.e., a matrix having both negative and non-integer entries. An example of a well-known filter that can be applied here is a "ramp filter." A ramp filter can be a finite impulse response (FIR) filter used in filtered reprojection image reconstruction algorithm in order to correct image intensity peaking in the center of the image. Ramp filters may be useful in removing the peak in dose distribution resulting from the EGRT dose delivery. It is understood that other filter types may be employed. Alternatively, filtering of the sinogram matrix can be modified to result in an integer-valued matrix instead of a real-valued matrix.

PET images are normally formed after collecting a large number of LORs, on the order of millions of LORs (collected over a few minutes). In EGRT delivery, the radiation response is delivered based on a small number of LORs, collected over a time window interval. The duration of the minimum time window interval can be equivalent to the maximum time it takes the system to respond to a LOR pattern. Alternatively, the time window interval can be less than this duration. One factor that may affect the duration of the maximum time window interval is the speed of the moving target volume. For example, if the target volume is stationary, then the duration of the time window interval can be longer. In some variations, the time window interval for EGRT is about (or no longer than) the amount of time it takes the target volume to move about 1 cm. The time window interval can range from about 0.5 seconds to about 60 seconds. For example, the time window interval can be about 0.5 seconds, about 1 second, about 2 seconds, about 3 seconds, about 4 seconds, about 5 seconds, about 10 seconds, about 15 seconds, about 20 seconds, about 25 seconds, about 30 seconds, about 35 seconds, about 40 seconds, about 45 seconds, about 50 seconds, about 55 seconds, or about 60 seconds. Another factor that may affect the duration of the maximum time window interval is the number of LORs desired to be processed since with a shorter time window interval fewer LORs are detected, and thus more patterns can be enabled for processing.

A sinogram corresponding to limited time window data can be referred to as a partial sinogram. A full sinogram comprising a plurality of partial sinograms is a linear sum of the partial sinograms. Since a full sinogram is the sum of a plurality of partial sinograms, applying a filter to the full sinogram may be equivalent to applying a filter to each partial sinogram and then adding them up. Thus, if the effect of a filter on a full sinogram is known, that information can be used to select an appropriate filter to apply to the partial sinograms. To explain, a full sinogram (collected over a period of time) as indicated below is S. Over time, it is collected as a series of partial sinograms S_i. Accordingly, $S=S0+S1+\ldots+Sk$ and $F(S)=F(S0+S1+\ldots+Sk)=F(S0)+F(S1)+\ldots+F(Sk)$. In some variations of the method, a linear filter such as a FIR filter may be applied to a partial sinogram.

When a partial sinogram ("sinogram P") of detected LORs is generated, response paths can also be represented as a sinogram matrix, although the geometry of the bins must generally match the physical characteristics of the treatment beam, rather than the PET detectors. The population of LORs can be binned into parallel beam sinograms, but given that treatment beams emanate from single source point inside the linear accelerator, in some instances it may be beneficial to use a sinogram having fan-beam geometry. Noting that binning geometry might differ, radiation response paths can be organized into a series of "beamlets," binned into a beamlet sinogram ("sinogram B"). Accordingly, generating radiation response paths becomes a mapping of sinogram P onto sinogram B.

The possible mappings can include: 1) if binning geometry is same, B=P; 2) if geometry is different, B=rebin(P). This approach may be useful because the resulting response sinogram B is weighted, i.e., each entry is not simply 0 or 1. This further handles the case of responding to N collinear LORs with N units of dose. Thus, in some variations, for each LOR pattern detected in sinogram P, a prescribed pattern in sinogram B is created. The detected patterns and radiation responses can be those outlined for FIGS. 3A-3C. However, it is understood that other patterns can be detected as well as other radiation responses delivered.

Figure 4:
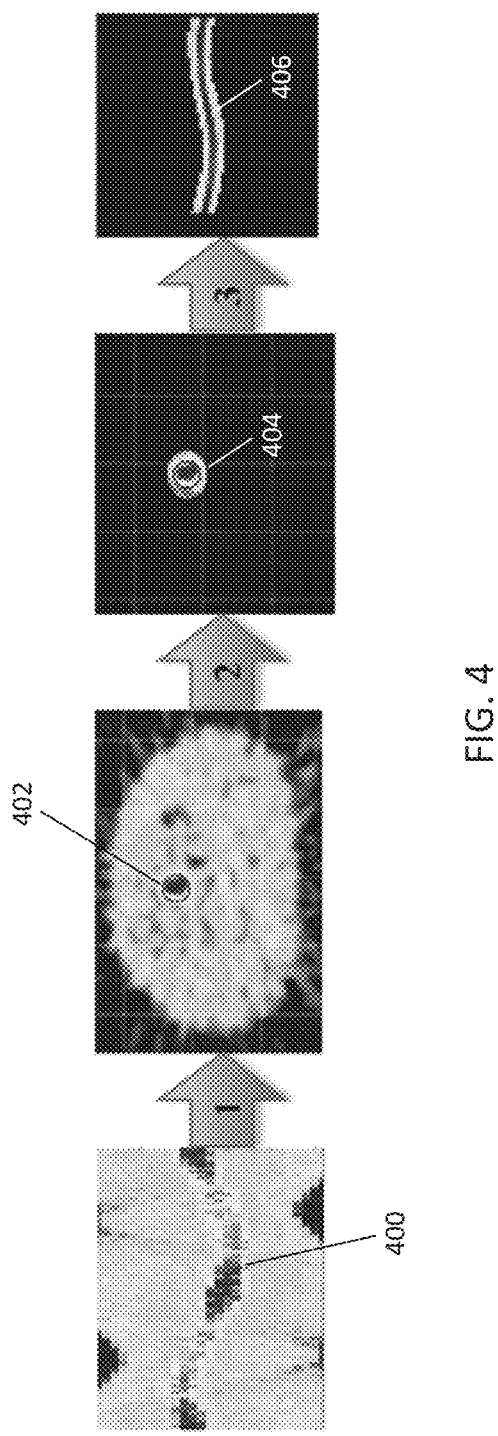
FIG. 4 depicts an exemplary method of forming a sinogram by reprojecting LORs.

When the general pattern is an arbitrary collection of LORs in sinogram P, in some variations, rather than looking for simple individual patterns, the entirety of P is processed in a single pass. For example, as shown in FIG. 4, the processing can be based on imaging theory. First, given sinogram P, reconstruction (via filtered reprojection or any other standard PET image reconstruction algorithm) of the corresponding image (400) is performed. Since sinogram P is only a partial sinogram, image (400) can be deemed only a partial image (e.g., 402), and mathematically each pixel in the image (402) gives a probability of LORs originating from within its bounds. Thus, the image (402) can be truncated to a PTV (planned tumor volume) region (404). By forward projecting the PTV region (404), a treatment beam sinogram (sinogram B, 406) can be generated.

Filtering the partial sinogram, whether linear or not, will yield a general real matrix, which can have negative values. Delivering both negative and fractional values can pose a challenge given that each radiation response is an equal unit of dose. Thus, in some variations, the EGRT method can be designed so that not all treatment beams are immediately delivered. For example, an intermediate buffer (U) can be introduced that holds the set of desired beamlets to be delivered. U can have fractional and negative values. Such a method may work as follows:

1) Initialize U=0
2) Repeat
   a. Obtain new desired radiation response paths in B
   b. Accumulate U=U+B
   c. Deliver as much dose in U as possible and update U=U−delivered dose If the EGRT system is able to deliver the entire radiation response, it does so, updating U by subtracting the delivered response. However, if the full response cannot be delivered, then a partial response is then delivered, and U is updated accordingly by subtracting the partial response. This type of delivery scheme may be useful since it allows for processing of negative entries in U. Although they are not immediately deliverable, negative entries can stay in the matrix until they are cancelled out (i.e., delivered) by a subsequent update.

Additional methods for delivering radiation using an intermediate buffer (U) can include without limitation, dose modulation using oversampled firing positions (treating k neighboring firing positions as a single one, can deliver up to k beamlets from such a combined firing position); dose modulation using linac control to vary the number of delivered pulses (delivering k pulses from a firing position); time lag modulation, to deliver radiation from opposing angles to boost beamlet dose; time lag modulation where the radiation is delivered over multiple gantry revolutions; use of parallel-beam space filters to deliver radiation from other firing positions; and dose modulation using a multi-leaf collimator in a non-binary way (e.g., firing during leaf transition).

Figure 5:
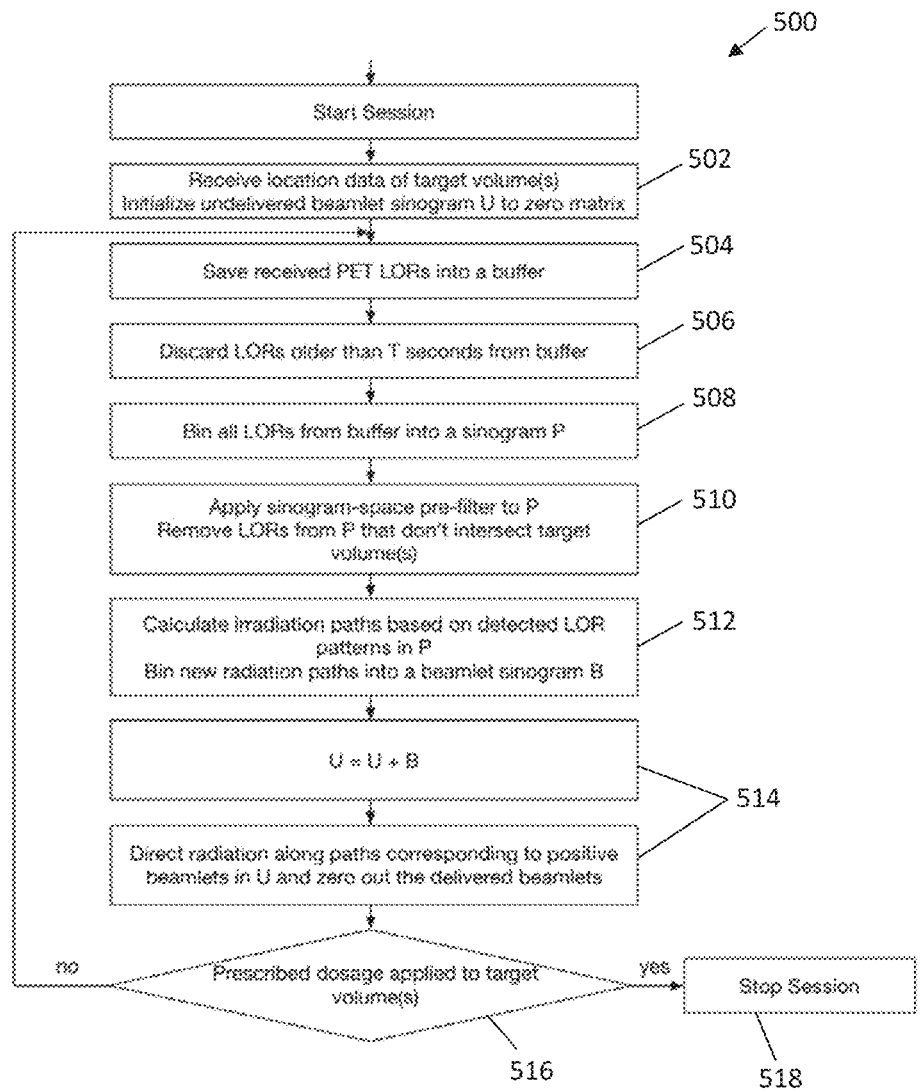
FIG. 5 is a flowchart illustrating an exemplary method for delivering radiation to a subject that includes filtering.

An exemplary method for delivering radiation to a target volume that includes filtering is illustrated in FIG. 5. Referring to the figure, method (500) includes receiving location data of the target volume(s) and initializing undelivered beamlet sinogram U to a zero matrix (502); saving detected LORs into a buffer (504); discarding LOR older than T seconds from the buffer (506); binning all LORs from the buffer into a sinogram P (508); applying a filter to sinogram P and removing LORs from sinogram P that do not intersect the target volume(s) (510); calculating radiation response paths (irradiation paths) based on the detected LOR patterns in sinogram P and binning new radiation paths into a beamlet sinogram B (512); and delivering radiation along paths corresponding to positive beamlets in U and zeroing out the delivered beamlets, as well as updating U with each delivered partial response (514). The radiation dosage delivered to the target volume is then recorded and a prescribed dosage determined (516). If the prescribed dosage has been met, then the treatment session is terminated (518). However, if the prescribed dosage has not been met, then the treatment session is continued and steps (504), (506), (508), (510), (512), (514), and (516) are repeated. It is understood that one or more steps can be repeated in order to obtain the prescribed dosage.

The methods for radiation delivery may be performed by an EGRT system comprising a circular gantry; a radiation source mounted on the gantry; a plurality of positron emission detectors mounted on the gantry, where the positron emission detectors detect the population of positron emission paths; and a controller in communication with the radiation source and the positron emission detectors. The radiation source may be positioned by rotating the gantry, and in some variations, the gantry may be continuously rotated. Furthermore, the methods may include the input of processing parameters and other system functions via a user interface.

The methods can be used alone or in conjunction with surgery, chemotherapy, radiosensitizers, and/or brachytherapy for the treatment of tumors. Some variations of tumor treatment plans may comprise surgically removing a portion of the tumor, and treating any remaining tumor masses with chemotherapy and/or EGRT. The various therapies in a tumor treatment plan may be determined in part by the size, type, location, progression and etiology of the tumor(s), as well as a variety of patient variables (e.g., gender, age, allergies, tolerance to certain pharmacological agents, etc.).

The radiation may be delivered to various target volumes, including but not limited to, tumor tissue, non-tumor tissue, cancers, other tissues or structures, body organs, or any region or volume that emits positrons (e.g., PET-avid regions), stationary regions or volumes, moving regions or volumes, or any region or volume identified by a user or practitioner (e.g., a planning target volume) or a machine algorithm (e.g., an image processing algorithm), and the like.

EGRT may be used alone or in conjunction with other types of radiation therapies. For example, EGRT may be used with intensity modulated radiation therapy (IMRT) and/or image guided radiation therapy (IGRT). IMRT may be capable of generating highly conformal dose distributions to deliver radiation to a targeted tumor region while sparing healthy tissues. IGRT may use imaging modalities such as MM or CT in pre-treatment planning to locate the tumor(s) within the patient. Combining either or both of these imaging modalities with EGRT may be useful for real-time location tracking of the targeted tumor region to help ensure that the therapeutic radiation is directed to the intended tissue region.

Tracking to Improve Delivery of EGRT

Further described herein are methods for improving delivery of EGRT by employing various target volume tracking processes. In one variation, tracking quality can be improved by using predicted or expected target motion speed to update the parameters of EGRT delivery. With this method, the time window can be increased or decreased based on the estimated target motion speed, which can be specified during the treatment planning process. Estimated motion speed can generally be determined based on the location of the target volume within the subject's body. For example, if the target volume is within the lung, the motion speed will correlate to the respiratory rate of the subject. If the target volume is within the brain, no motion at all is expected, and the motion speed can be set to zero.

When the location of a target volume is to be more precisely identified by tracking respiration (breathing) movements of the subject, the methods for EGRT may include tracking the location of tumors in real time, and/or include delivering a desired dose of radiation to tumor(s) in a planning target volume (PTV) while sparing peripheral tissue. A PTV may be determined during a pre-treatment and/or planning session by a physician and/or technician (e.g., radiation oncologist, medical physicist, radiologist, radiation therapist, etc.) using a variety of imaging modalities, such as CT, PET, MM, x-ray, etc., either alone or in combination. A PTV may also be determined during a radiation therapy session. For example, a PTV may be determined periodically during a radiation therapy session using one or more types of on-board imaging modalities (e.g., CT, PET, MRI, X-ray, etc.), either alone or in combination. Data pertaining to a PTV may be stored in the microprocessor of an EGRT system for use by a medical physicist and/or radiation therapist during the radiation therapy session. A PTV may include the tumor region and peripheral non-tumor tissue in the region of the tumor region, or a PTV may include only the tumor region without the peripheral non-tumor tissue. Alternatively or additionally, a PTV may include the visible location and growth of a tumor as determined by a selected imaging modality (e.g., CT, PET, MRI, X-ray, SPECT, etc.). In some cases, a PTV may include a PET-avid tissue region (i.e., a tissue volume that has taken up PET tracer and is emitting photons resulting from positron annihilations), and in other cases, a PTV may include both the PET-avid region and adjacent non-PET-avid tissue regions. In some variations, a PTV may include the regions described above with one or more additional margins, for example, margins for patient and/or organ motion, organ shape and size variation, and uncertainties in radiation beam alignment.

Traditional IMRT (intensity-modulated radiation therapy) and SBRT (stereotactic body radiation therapy) radiation therapies specify a gross tumor volume (GTV) and a planned tumor volume (PTV) where the GTV represents the actual tumor volume and the PTV includes all of the volume necessary to guarantee that the GTV is covered when all of the misalignments and system errors are taken into account. As shown in FIG. 6A, PTV's are generally 5 to 10 mm larger than GTV's when the tumor volumes are stationary (no motion). However, when motion is considered, the PTV size is typically increased by at least the range of motion of the tumor. The bulk of tumor motion thus stems from the subject's breathing cycle. For example, referring to FIGS. 6B-6D, the PTV with motion taken into account is shown, as well as movement of the location or position of the GTV within the boundaries of the PTV (with motion) at different time points during the breathing cycle.

Radiotherapy has traditionally focused on reducing the dose to healthy tissue while maintaining dose to the GTV. Improvements have come about from increasing the number of angles of delivery, improving the resolution of the actual high energy radiation, and reducing target margins, that is reducing the size of the PTV. Reducing the PTV is particularly difficult for those cases where breathing causes the GTV to move. Ideally, the radiotherapy system could track the GTV and respond with directed radiation in real-time. However, there are a number of practical limitations to this that include increased dose to the patient from imaging the GTV, positional accuracy of the GTV tracking, and temporal resolution of the GTV tracking.

As an alternative to reducing the dose to healthy tissue by tracking the GTV real-time, it may also be possible to reduce the dose to healthy tissue by narrowing the window in which the GTV is located without knowing the exact, real-time location of the GTV. By narrowing the window in which the GTV is located, an algorithm can be used to identify the PTV in real-time. Depending on the confidence in the real-time tracking of the GTV, both the extent to which the PTV window is narrowed and the weighting of the new PTV may be varied. For example, if there was complete confidence in the real-time location of the GTV, then the PTV may be shrunk nearly to the GTV extents itself. On the other extreme, if there is little to no confidence, then the original PTV that covered the entire movement envelope plus margins may be used. In a more practical case, the instantaneous location of the GTV may be constrained to a portion of the PTV (original, without motion), e.g., the upper half of the original PTV with a confidence of about 90% to about 99% at a particular projection. For this projection the effective, real-time PTV (ERT PTV) may be shrunk to only the upper half of the original.

The confidence weighting may be a threshold that sets the window of the ERT PTV. The ERT PTV can be shrunk from the original until the confidence of locating the GTV within that window would fall below a set confidence level, e.g., fall below a confidence level of about 90% to about 99%. In some variations, the confidence level can be set to 90%. In other variations, the confidence level can be set to 91%, 92%, 93%, 94%, 95%, 96%, 97% or 98%. In yet further variations, the confidence level can be set to 99%.

The ability to track the tumor real-time to some level that allows shrinking the ERT PTV can be accomplished by methods that give information about the actual GTV location (e.g., by imaging the GTV) or that gives information about the breathing cycle and other movements of the patient. For example, as illustrated in FIGS. 6B-6D, movement of the GTV can be tracked by noting the position of the GTV at different time points during the breathing cycle. FIG. 6B shows GTV position at a first time point and the corresponding ERT PTV, FIG. 6C shows GTV position at a second time point and the corresponding ERT PTV, and FIG. 6D shows GTV position at a third time point and the corresponding ERT PTV. With better the tracking, higher confidence levels can be set, resulting in a smaller ERT PTV and increased amount of healthy tissue that can be spared.

The methods for providing GTV motion from patient movement and breathing motion may include the use of internal fiducials, external fiducials, PET imaging, MR imaging, external x-ray imaging, or other imaging methods. The tracking mechanisms do not necessarily need to track the GTV directly, but could just track the breathing motion. The method may include obtaining a 4D imaging scan of the subject prior to the radiation treatment. Then the phase of the subject's breathing cycle may be correlated to a shrunken PTV window that includes the GTV. Breathing motion can be tracked using bite guards, breathing straps, pressure sensors, accelerometers, external imaging systems, or chest wall or diaphragm tracking using an imaging system such as PET, MR, or x-rays.

The invention claimed is:

1. A method for delivering radiation to a subject comprising:
   detecting a population of positron emission paths;
   detecting a pattern of positron emission paths within the population;
   determining one or more response paths based at least in part on processing of the pattern, wherein the one or more response paths is not collinear to any positron emission path from the detected pattern; and
   delivering radiation along the one or more response paths to a target volume within the subject.

2. The method of claim 1, wherein the pattern comprises collinear positron emission paths.

3. The method of claim 1, wherein the pattern comprises non-intersecting position emission paths.

4. The method of claim 1, wherein the pattern comprises positron emission paths that intersect at a point within the target volume.

5. The method of claim 1, wherein the pattern comprises positron emission paths that intersect within the target volume to define a target area within the target volume.

6. The method of claim 1, wherein the pattern comprises an arbitrary set of positron emission paths that intersect the target volume.

7. The method of claim 1, wherein at least two response paths are collinear with a positron emission path from the detected pattern.

8. The method of claim 1, wherein processing of the pattern comprises calculating the one or more response paths based on one or more detected positron emission paths in the pattern.

9. The method of claim 1, wherein processing of the pattern comprises assigning a weight to the one or more response paths, the weight correlating to a radiation dose delivered along the one or more response paths.

10. The method of claim 9, wherein the assigned weight has a negative value.

11. The method of claim 1, wherein processing of the pattern comprises calculating a weight of a set of response paths, the weight being proportional to the number of positron emission paths in the detected pattern.

12. The method of claim 1, wherein processing of the pattern comprises calculating a set of weighted response paths via a reprojection procedure.

13. The method of claim 1, wherein processing of the pattern comprises binning the population of positron emission paths into a sinogram matrix.

14. The method of claim 13, further comprising filtering the sinogram matrix.

15. The method of claim 14, wherein filtering comprises applying a finite impulse response (FIR) filter to the sinogram matrix.

16. The method of claim 14, wherein filtering comprises applying a linear or non-linear filter to the sinogram matrix.

17. The method of claim 1, further comprising recording a dose of radiation delivered along the one or more response paths.

18. The method of claim 1, further comprising recording one or more undelivered response paths, the undelivered response paths having a negative weight, and adding the negative weight to a weight of subsequently determined response paths.

19. The method of claim 1, further comprising filtering the population of positron emission paths.

20. The method of claim 1, further comprising repeating radiation delivery until a predetermined dose of radiation is received by the target volume.

21. The method of claim 1, further comprising tracking motion speed of the target volume.

22. The method of claim 21, wherein tracking motion speed of the target volume comprises tracking the respiratory rate of the subject.

23. The method of claim 21, wherein tracking motion speed of the target volume reduces the size of a planned tumor volume (PTV) or an effective, real-time planned tumor volume (ERT PTV).

24. The method of claim 1, wherein the method is performed by a system comprising:
- a circular gantry;
- a radiation source mounted on the gantry;
- a plurality of positron emission detectors mounted on the gantry, wherein the plurality of positron emission detectors detect the population of positron emission paths; and
- a controller in communication with the radiation source and the positron emission detectors.

25. The method of claim 24, wherein the controller is configured to process the pattern and determine the one or more response paths.

26. The method of claim 24, wherein the controller is configured to position the radiation source with respect to the one or more response paths.

27. The method of claim 26, wherein the radiation source is positioned by rotating the gantry.

28. The method of claim 25, wherein delivering radiation along the one or more response paths to the target volume occurs from opposite sides of the gantry.

29. The method of claim 25, wherein delivering radiation along the one or more response paths to the target volume occurs from various positions on the gantry.

30. The method of claim 25, wherein the target volume is PET-avid.

* * * * *